US012625077B2

(12) United States Patent
Zimmerman

(10) Patent No.: US 12,625,077 B2
(45) Date of Patent: May 12, 2026

(54) FLUOROSURFACTANT DETECTION

(71) Applicant: OHIO NORTHERN UNIVERSITY, Ada, OH (US)

(72) Inventor: Jake R. Zimmerman, Ada, OH (US)

(73) Assignee: OHIO NORTHERN UNIVERSITY, Ada, OH (US)

( * ) Notice: Subject to any disclaimer, the term of this patent is extended or adjusted under 35 U.S.C. 154(b) by 616 days.

(21) Appl. No.: 18/167,945

(22) PCT Filed: Aug. 13, 2021

(86) PCT No.: PCT/US2021/045925
§ 371 (c)(1),
(2) Date: Feb. 13, 2023

(87) PCT Pub. No.: WO2022/036205
PCT Pub. Date: Feb. 17, 2022

(65) Prior Publication Data
US 2024/0310281 A1 Sep. 19, 2024

Related U.S. Application Data

(60) Provisional application No. 62/706,413, filed on Aug. 14, 2020.

(51) Int. Cl.

| | |
|---|---|
| ***G01N 21/00*** | (2006.01) |
| ***G01N 21/64*** | (2006.01) |
| ***G01N 21/94*** | (2006.01) |
| *G01N 21/77* | (2006.01) |
| *G01N 21/84* | (2006.01) |
| *G01N 33/24* | (2006.01) |

(52) U.S. Cl.
CPC ........... *G01N 21/643* (2013.01); *G01N 21/94* (2013.01); *G01N 2021/6439* (2013.01); *G01N 2021/7759* (2013.01); *G01N 2021/7786* (2013.01); *G01N 2021/8472* (2013.01); *G01N 33/24* (2013.01)

(58) Field of Classification Search
CPC .................................................... G01N 21/643
USPC ......................................................... 436/126
See application file for complete search history.

(56) References Cited

U.S. PATENT DOCUMENTS

| | | | | |
|---|---|---|---|---|
| 5,965,736 | A | 10/1999 | Akhavan-Tafti | |
| 2016/0041330 | A1 | 2/2016 | Chen et al. | |
| 2017/0241969 | A1 * | 8/2017 | Zimmerman .......... | G01N 21/64 |

OTHER PUBLICATIONS

International Search Report and Written Opinion issued Dec. 28, 2021 in PCT/US2021/045925, 11 pages.
Fang et al., "Aggregated-fluorescent detection of PFAS with a simple chip," Nov. 2018, Analytical Methods, vol. 11, Issue 2, Abstract, 5 pages.

* cited by examiner

*Primary Examiner* — Elizabeth A Robinson
*Assistant Examiner* — Emily R. Berkeley
(74) *Attorney, Agent, or Firm* — Vorys, Sater, Seymour and Pease LLP; Rex W. Miller, II

(57) ABSTRACT

A method may comprise: exposing a substituted chromone dissolved in a solvent to a sample; taking a fluorescence measurement of the sample after exposure to the substituted chromone; and determining a presence or absence of one or more ions in the sample, a concentration of the one or more ions in the sample, or both based on the fluorescence measurement.

23 Claims, 12 Drawing Sheets

FLUOROSURFACTANT DETECTION

CROSS-REFERENCE TO RELATED APPLICATIONS

The present invention is a national stage application of pending International Patent Application No. PCT/US2021/045925 filed Aug. 13, 2021, which claims the benefit of U.S. Provisional Patent Application No. 62/706,413 filed Aug. 14, 2020, which are incorporated by reference herein in their entirety.

FIELD OF THE INVENTION

This invention relates to a new class of fluorophores that, in some instances, shifts emission wavelength upon interaction of per- and poly-fluoroalkyl substances (PFASs). The fluorophores are useful for, for example, detecting the presence of PFASs in field samples.

BACKGROUND

Once heralded as wonder chemicals, PFASs are now better known for their persistence in the environment and their bioaccumulation, contaminating water and soil and subsequently exerting toxic effects. The extent of PFAS contamination is currently unknown, and clean-up efforts are hampered because of the difficulty in detecting the compositions. Currently, samples must be removed from the site and sent to laboratories with sophisticated instrumentation to determine the presence of PFASs. Thus, a test for PFASs that is faster and less expensive is sought after, particularly a test that could be used in the field.

BRIEF SUMMARY

In some instances, a method of detecting PFASs may comprise exposing a substituted chromone according to Compound 1 to a sample. Subsequently, the method comprises taking a fluorescence measurement of the sample after exposure to the substituted chromone and determining a presence or absence of one or more per- or polyfluoroalkyl hydrocarbons (PFAS), a concentration of the one or more PFAS in the sample, or both based on the fluorescence measurement. $R_1$ of Compound 1 is methyl acetate, methoxy, or methyl (2,2-dimethyl) acetate. $R_2$ is 4-methylbenzoyl, 4-methoxybenzoyl, naphthalene-1-carbonyl, naphthalene-2-carbonyl, 4-phenylbenzoyl, or a perfluoroalkyl sulfonic acid compound wherein the alkyl is $C_5$-$C_{12}$. $R_3$ is hydrogen, methoxy, bromo, chloro, fluoro, methyl, ethyl, or isopropyl; $R_4$ is hydrogen, methoxy, bromo, chloro, fluoro, methyl, ethyl, or isopropyl. $R_5$ is hydrogen, methoxy, bromo, chloro, fluoro, methyl, ethyl, or isopropyl. $R_{6a-e}$ are any of hydrogen, methoxy, bromo, chloro, fluoro, methyl, ethyl, or isopropyl.

Compound 1

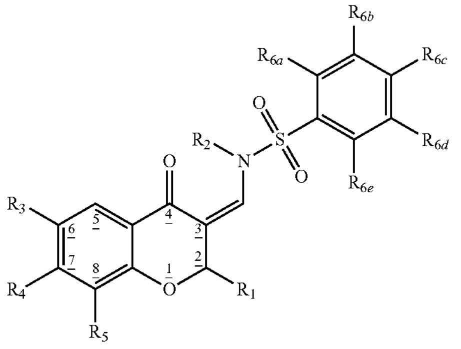

In some instances, a method of detecting PFASs may comprise exposing a substituted chromone according to Compound 2 to a sample. Subsequently, the method comprises taking a fluorescence measurement of the sample after exposure to the substituted chromone and determining a presence or absence of one or more per- or polyfluoroalkyl hydrocarbons (PFAS), a concentration of the one or more PFAS in the sample, or both based on the fluorescence measurement. $R_1$ of Compound 2 is methyl acetate, methoxy, or methyl (2,2-dimethyl) acetate. $R_2$ is 4-methylbenzoyl, 4-methoxybenzoyl, naphthalene-1-carbonyl, naphthalene-2-carbonyl, 4-phenylbenzoyl, or a perfluoroalkyl sulfonic acid compound wherein the alkyl is $C_5$-$C_{12}$, $R_3$ is hydrogen, methoxy, bromo, chloro, fluoro, methyl, ethyl, or isopropyl, $R_4$ is hydrogen, methoxy, bromo, chloro, fluoro, methyl, ethyl, or isopropyl, $R_5$ is hydrogen, methoxy, bromo, chloro, fluoro, methyl, ethyl, or isopropyl. $R_{6a-e}$ are any of hydrogen, methoxy, bromo, chloro, fluoro, methyl, ethyl, or isopropyl.

Compound 2

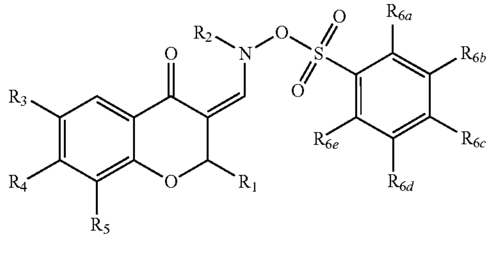

In some instances, a method of detecting PFASs may comprise exposing a substituted chromone according to Compound 3 to a sample, taking a fluorescence measurement of the sample after exposure to the substituted chromone, and determining a presence or absence of one or more per- or polyfluoroalkyl hydrocarbons (PFAS), a concentration of the one or more PFAS in the sample, or both based on the fluorescence measurement. $R_1$ is methyl acetate, methoxy, or methyl (2,2-dimethyl) acetate. $R_2$ is 4-methylbenzoyl, 4-methoxybenzoyl, naphthalene-1-carbonyl, naphthalene-2-carbonyl, 4-phenylbenzoyl, or a perfluoroalkyl sulfonic acid compound wherein the alkyl is $C_5$-$C_{12}$. $R_3$ is hydrogen, methoxy, bromo, chloro, fluoro, methyl, ethyl, or isopropyl. $R_4$ is hydrogen, methoxy, bromo, chloro, fluoro, methyl, ethyl, or isopropyl. $R_5$ is hydrogen, methoxy, bromo, chloro, fluoro, methyl, ethyl, or isopropyl. $R_{6a-e}$ are any of hydrogen, methoxy, bromo, chloro, fluoro, methyl, ethyl, or isopropyl.

Compound 3

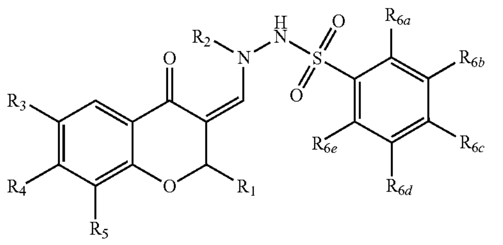

In some instances, a PFAS detecting composition may comprise Compound 1, above, where $R_1$ is methyl acetate, methoxy or methyl (2,2-dimethyl) acetate. $R_2$ is 4-methylbenzoyl, 4-methoxybenzoyl, naphthalene-1-carbonyl, 4-phenylbenzoyl, a perfluoroalkyl sulfonic acid compound wherein the alkyl is $C_5$-$C_{12}$. $R_3$ is hydrogen, methoxy, bromo, chloro, fluoro, methyl, ethyl, or isopropyl. $R_4$ is hydrogen, methoxy, bromo, chloro, fluoro, methyl, ethyl, or isopropyl. $R_5$ is hydrogen, methoxy, bromo, chloro, fluoro, methyl, ethyl, or isopropyl. $R_{6a-e}$ is any of hydrogen, methoxy, bromo, chloro, fluoro, methyl, ethyl, or isopropyl.

DETAILED DESCRIPTION

Figure 1:
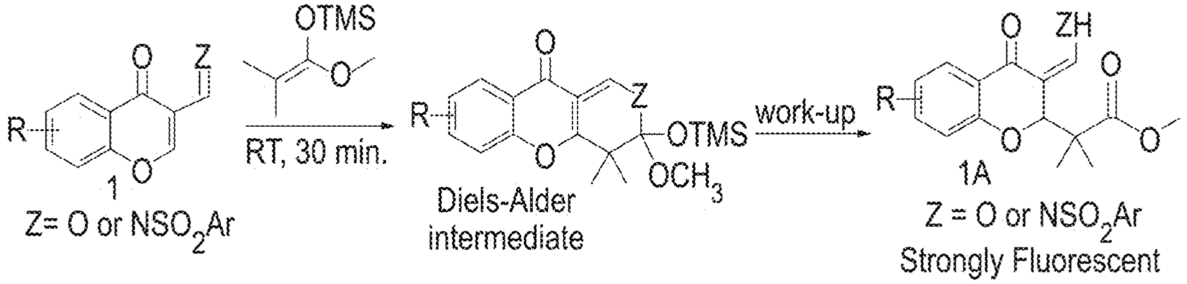
FIG. 1 illustrates an inverse electron demand hetero-Diels-Alder (HDA) reaction useful for producing at least some of the fluorophores described herein.

The present disclosure relates to a new class of fluorophores suitable for the detection of per- and poly-fluoroalkyl substances (PFASs) based on a chromone structure, where the synthesis may include an inverse electron demand hetero-Diels-Alder (HDA) reaction from readily available materials such as silyl enol ethers and substituted 3-formyl chromones. The structure of the fluorophores is designed with the flexibility to have multiple substituents to the base chromone structure. By altering the chemical composition and location of the substituents, the properties of the substituted chromone may be adjusted including, but not limited to, a peak absorption wavelength, and a peak emission wavelength.

Compound 1 illustrates a general structure for a substituted chromone of the present disclosure. More specifically, Compound 1 has a chromone structure with substitutions in the 2 position ($R_1$), optionally the 6 position ($R_3$), optionally the 7 position ($R_4$), and optionally the 8 position ($R_5$), additionally the chromone structure has substitutions in the 3 position, as depicted in the structure below, further comprising a substitution off of a nitrogen, and a carbon ring with substitutions optionally on each carbon of the ring ($R_{6a}$ through $R_{6e}$). Accordingly, for Compound 1, $R_1$ may be methyl acetate, methoxy, or methyl (2,2-dimethyl) acetate; $R_2$ may be 4-methylbenzoyl, 4-methoxybenzoyl, naphthalene-1-carbonyl, naphthalene-2-carbonyl, 4-phenylbenzoyl, or a perfluoroalkyl sulfonic acid compound wherein the alkyl is $C_5$-$C_{12}$; $R_3$ may be hydrogen, methoxy, bromo, chloro, fluoro, methyl, ethyl, or isopropyl; $R_4$ may be hydrogen, methoxy, bromo, chloro, fluoro, methyl, ethyl, or isopropyl; $R_5$ may be hydrogen, methoxy, bromo, chloro, fluoro, methyl, ethyl, or isopropyl; and $R_{6a-e}$ may each be any of hydrogen, methoxy, bromo, chloro, fluoro, methyl, ethyl, or isopropyl.

Compound 1

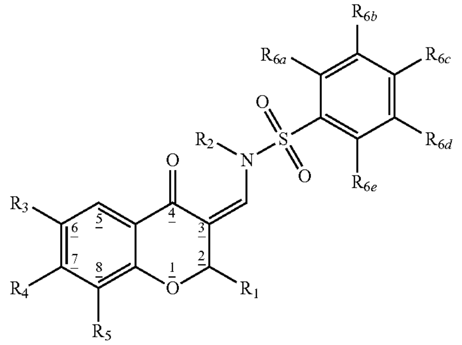

More specifically, Compounds 1b-4 provide general structures of the substituted chromones of Compound 1 with the $R_2$ group specified: Compound 2: $R_2$ is hydroxymethylene, and Compound 3: $R_2$ is (4-methylphenylsulfonamido) methylene.

Compound 2

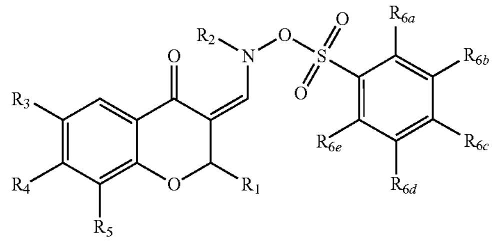

Compound 3

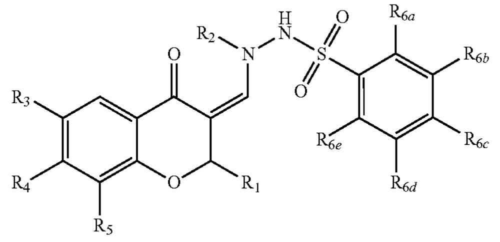

Specific exemplary substituted chromones suitable for use in the methods, kits, systems, and compositions described herein are illustrated in Table 1. It should be noted that the specific embodiments of Table 1 are intended to be exemplary, and are in no way limiting to the scope of Compound 1.

TABLE 1

| | Name | Structure |
|---|---|---|
| Compound 4 | methyl (Z)-2-(6-methoxy-3-((N-((4-methoxyphenyl)sulfonyl)-[1,1'-biphenyl]-4-carboxamido)methylene)-4-oxochroman-2-yl)-2-methylpropanoate | 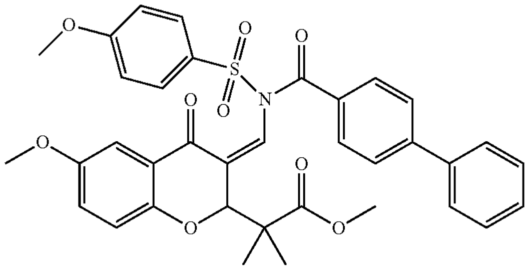 [SMILES: COC(=O)C(C)(C)C1Oc2ccc(OC)cc2C(=O)/C1=C\N(C(=O)c1ccc(-c2ccccc2)cc1)S(=O)(=O)c1ccc(OC)cc1] |
| Compound 5 | methyl (Z)-2-(6-fluoro-3-((N-((4-methoxyphenyl)sulfonyl)-4-methylbenzamido)methylene)-4-oxochroman-2-yl)-2-methylpropanoate | 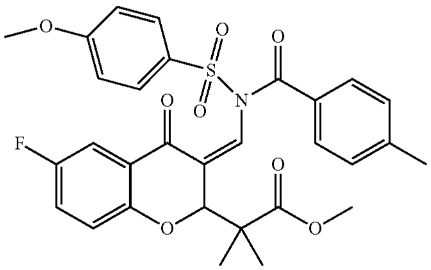 |
| Compound 6 | methyl (Z)-2-(6-fluoro-3-((N-((4-methoxyphenyl)sulfonyl)-1-naphthamido)methylene)-4-oxochroman-2-yl)-2-methylpropanoate | 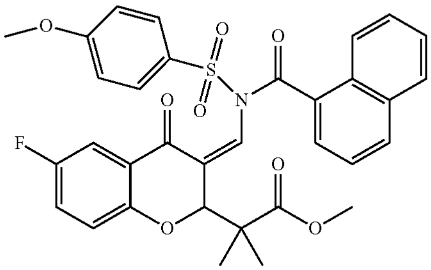 [SMILES: COC(=O)C(C)(C)C1Oc2ccc(F)cc2C(=O)/C1=C\N(C(=O)c1cccc2ccccc12)S(=O)(=O)c1ccc(OC)cc1] |
| Compound 7 | methyl (Z)-2-(3-(((4-methoxy-N-((perfluorooctyl)sulfonyl)phenyl) sulfonamido)methylene)-6-methyl-4-oxochroman-2-yl)-2-methylpropanoate | 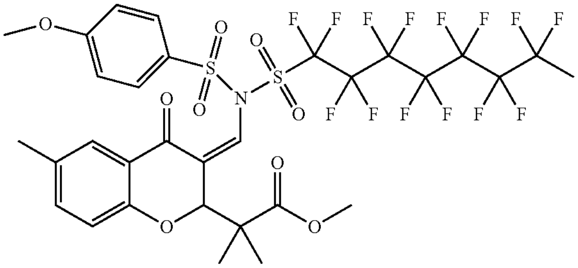 [SMILES: COC(=O)C(C)(C)C1Oc2ccc(C)cc2C(=O)/C1=C\N(S(=O)(=O)c1ccc(OC)cc1)S(=O)(=O)C(F)(F)C(F)(F)C(F)(F)C(F)(F)C(F)(F)C(F)(F)C(C)(F)F] |
| Compound 8 | methyl (Z)-2-(6-methyl-3-(((4-methoxyphenyl)sulfonamido) methylene)-4-oxochroman-2-yl)-2-methylpropanoate | 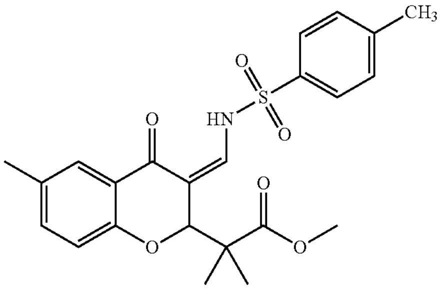 |

TABLE 1-continued

| | Name | Structure |
|---|---|---|
| Compound 9 | methyl (Z)-2-(6-methoxy-3-(((4-methoxyphenyl)sulfonamido) methylene)-4-oxochroman-2-yl)-2-methylpropanoate | 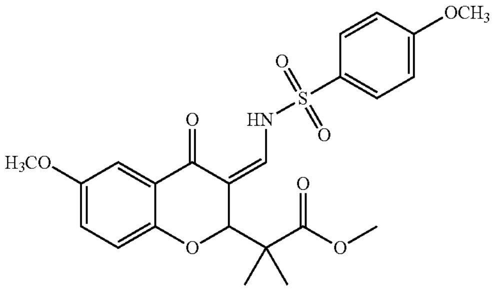 [SMILES: COC(=O)C(C)(C)C1Oc2ccc(OC)cc2C(=O)/C1=C\NS(=O)(=O)c1ccc(OC)cc1] |
| Compound 10 | methyl (Z)-2-(3-(((4-methoxyphenyl)sulfonamido) methylene)-4-oxochroman-2-yl)-2-methylpropanoate | 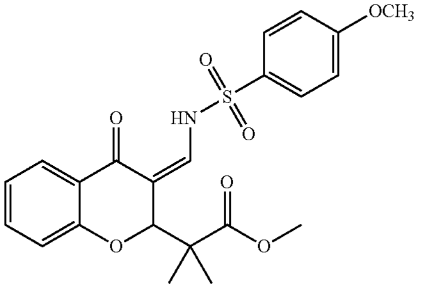 [SMILES: COC(=O)C(C)(C)C1Oc2ccccc2C(=O)/C1=C\NS(=O)(=O)c1ccc(OC)cc1] |
| Compound 11 | methyl (Z)-2-(6-methoxy-3-(((4-methoxyphenyl)sulfonamido) methylene)-4-oxochroman-2-yl) acetate | 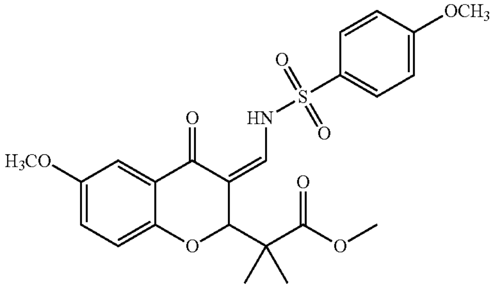 [SMILES: COC(=O)C(C)(C)C1Oc2ccc(OC)cc2C(=O)/C1=C\NS(=O)(=O)c1ccc(OC)cc1] |
| Compound 12 | methyl (Z)-2-(6-ethyl-3-(((4-methoxyphenyl)sulfonamido) methylene)-4-oxochroman-2-yl)-2-methylpropanoate | 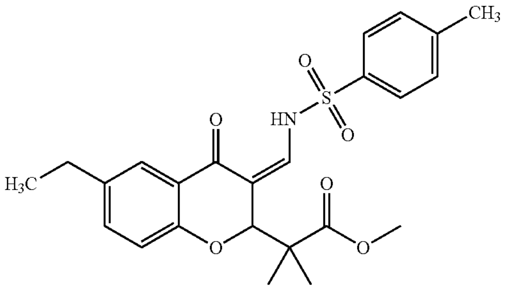 [SMILES: CCc1ccc2c(c1)C(=O)/C(=C\NS(=O)(=O)c1ccc(C)cc1)C(C(C)(C)C(=O)OC)O2] |

According to various embodiments, the substituted chromones of the present disclosure may be readily synthesized using organic chemistry techniques. FIGS. 1-2 illustrate various exemplary synthetic pathways that may be used to produce substituted chromones. An inverse electron demand hetero-Diels-Alder (HAD) reaction may be useful for producing at least some of the fluorophores described herein. It should be noted that the featured synthetic pathway embodiments are intended to be exemplary, and are in no way limiting to the scope of the synthetic pathway suitable for producing substituted chromones described herein.

FIG. 1 illustrates a general inverse-demand hetero-Diels-Alder (HDA) reaction useful for adding the $R_1$ group of Compound 1 of FIG. 1 to the 2 position of the chromone structure. Compound 1A of FIG. 1 is a chromone structure having substitution that is the precursor to the substituted chromone product of Compound 1 (e.g., an 4-methylbenzoyl for the $R_2$ group, or 4-methoxybenzoyl, naphthalene-1-carbonyl, naphthalene-2-carbonyl, 4-phenylbenzoyl, or a perfluoroalkyl sulfonic acid compound wherein the alkyl is $C_5$-$C_1$ an aldehyde for the $R_2$ group of hydroxymethylene or a sulfonamide; and for $R_{6a-e}$, optionally a hydrogen, methoxy, bromo, chloro, fluoro, methyl, ethyl, or isopropyl) and optionally substitution in the aromatic ring of the chromone corresponding to $R_3$, $R_4$, and/or $R_5$, depending on the desired substituted chromone product. Compound 1 of FIG. 1 is reacted with dimethylsilyl ketene acetal to produce a Diels-Alder intermediate shown as the intermediate structure of FIG. 1, which has a third ring structure added to the chromone structure. The initial reaction of FIG. 1 may be performed at room temperature (or an elevated temperature, e.g., up to about 50° C.) in a solvent like dichloromethane and/or tetrahydrofuran for about 10 minutes to about 2 hours. Upon workup, Compound 1A of FIG. 1, which correspond to some embodiments of Compound 1, is produced and isolated.

Figure 2A:
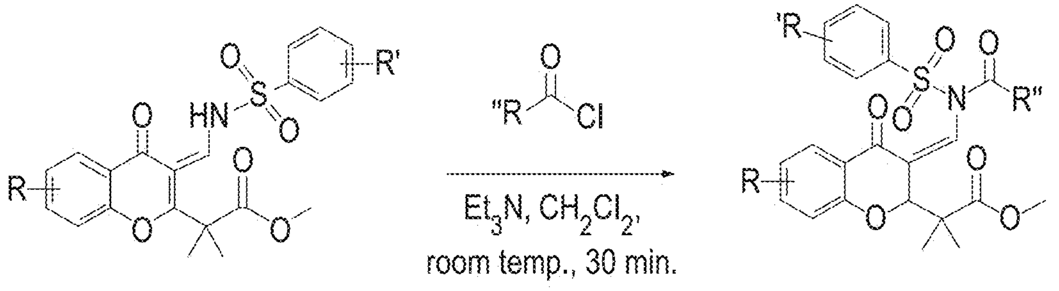
FIG. 2 illustrates an inverse electron demand HDA reaction for producing fluorophores as described herein.
Figure 2B:
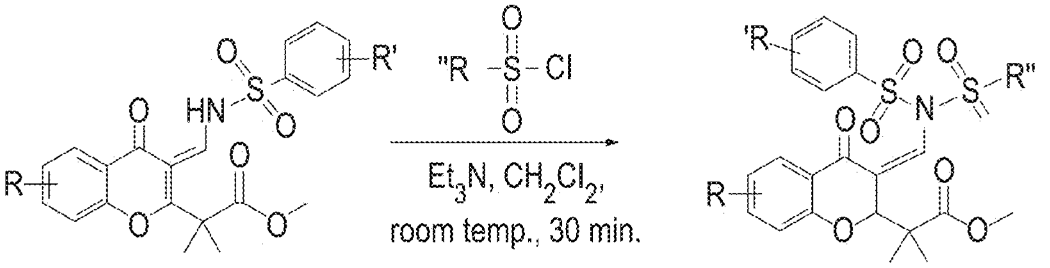

FIG. 2*a* and FIG. 2*b* illustrate specific inverse-demand hetero-Diels-Alder (HDA) reactions for fluorophore modification synthesis.

The substituted chromones of Compound 1 may have a peak absorption wavelength between about 300 nm and about 400 nm and a peak emission wavelength between about 420 nm and about 520 nm. Compound 4 may have a peak absorption wavelength between about 370 and about 440 nm and a peak emission wavelength between about 500 nm and about 540 nm.

In some embodiments, the substituted chromones of the present disclosure may form a complex with PFASs where complexing with the PFASs may cause a change in the peak emission wavelength and/or the emission intensity for a specific wavelength of the corresponding fluorescence. One or both of these fluorescent properties may be monitored to determine the presence of PFASs and/or the concentration of PFASs in a sample. Determination of the concentration of PFASs in the sample may be achieved by comparing fluorescent properties (e.g., the amount of and/or change to the peak emission shift and/or emission intensity) to a table, graph, color chart reference, or other mathematical representation (e.g., a mathematical formula) of a known correlation between concentration and the fluorescent properties.

The fluorescence of the substituted chromones is in the visible spectrum. Accordingly, the changes in peak emission wavelength may be detected visually upon excitation with a long wavelength UV-source (e.g., a 365 nm source) or other suitable excitation source that excites the substituted chromone, which may be at or near the peak absorption wavelength (e.g., at a wavelength between about 300 nm and about 450 nm). The color emitted may be used qualitatively to determine if a specific PFAS is present. Alternatively or in combination, the color emitted may be compared to reference samples or a color chart reference for a more quantitative analysis of ion concentration. For example, a color chart reference specific to the substituted chromone color change range may be used in a similar way a color chart reference is used with pH paper to qualitatively and/or quantitatively analyze a color change to pH paper.

Measuring the emission intensity may be performed in multiple ways, such as, by way of non-limiting example, using a fluorimeter such as a photodiode, phototransistor, avalanche photodiode, photoresistor, or a photomultiplier tube. In some instances, the emission intensity may be measured at the peak emission wavelength for each spectrum taken. Alternatively or in combination therewith, the emission intensity may be measured at a specific emission wavelength, which may be the peak emission wavelength substituted chromones without having PFASs present or at a specific wavelength where emission intensity varies with varying PFAS concentration. In some instances, the available hardware may dictate the methods available for implementation. For example, if a detector for a single wavelength or small window of wavelengths is available, analysis according to wavelength H may be required. In some instances, more than one of the foregoing methods may be implemented.

In some instances, the substituted chromones of the present disclosure may form a complex with PFASs. Exemplary PFASs may include, but are not limited to, perfluorooctanoic acid (PFOA), perfluoroheptanoic acid (PFHeptA), perfluoropentanoic acid (PFPentA), perfluorobutyric acidd (PFButyrA), perfluoropropionic acid (PFPropA), perfluorobutyric sulfonic acid (PFButyrS), perfluorooctanesulfonyl chloride (PFOS-Cl), undecafluoro-2-methyl-3-oxahexanoic acid, ammonium salt of hexafluoropropylene oxide dimer acid (HFPO-DA) fluoride, and the like, and any combination thereof. When interacting with a PFAS, the peak emission wavelength of the substituted chromones may shift, typically red-shift to longer wavelengths. The change in fluorescence properties (e.g., peak emission wavelength and/or emission intensity) may be correlated to a concentration of the PFASs. Structures of exemplary PFASs that form a complex with substituted chromones of the present disclosure may be found in Table 2.

TABLE 2

| Name | Structure |
|---|---|
| PFOA | 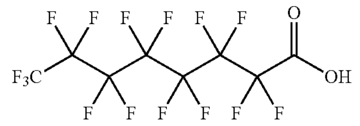 [SMILES: O=C(O)C(F)(F)C(F)(F)C(F)(F)C(F)(F)C(F)(F)C(F)(F)C(F)(F)F] |
| PFHeptA | 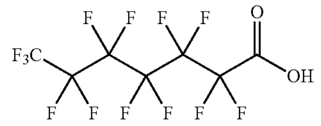 [SMILES: O=C(O)C(F)(F)C(F)(F)C(F)(F)C(F)(F)C(F)(F)C(F)(F)F] |
| PFPentA | 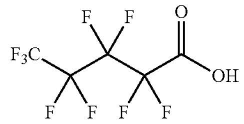 [SMILES: O=C(O)C(F)(F)C(F)(F)C(F)(F)C(F)(F)F] |
| PFButyrA | 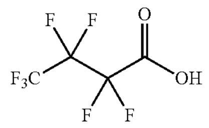 |
| PFPropA | 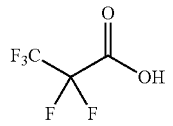 |
| PFButyrS | 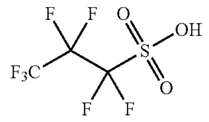 [SMILES: O=S(=O)(O)C(F)(F)C(F)(F)C(F)(F)F] |
| PFOS-Cl | 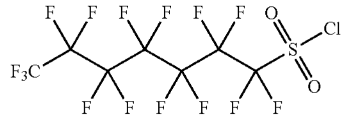 [SMILES: O=S(=O)(Cl)C(F)(F)C(F)(F)C(F)(F)C(F)(F)C(F)(F)C(F)(F)C(F)(F)F] |

The substituted chromones of Compound 1 may be dissolved or otherwise dispersed in a solvent at any suitable concentration to observe fluorescence visually or detect fluorescence with a fluorimeter, which, in some instances, may be a concentration of about 1 μM to about 5 μM, or the concentration may be higher depending on the substituted chromone or if detection is by visual means. In some embodiments, a kit, a method, or a system may utilize a stock solution of the substituted chromones described herein at a concentration of about 1 μM to about 5 μM, where for detection of PFASs and analysis of fluorescence the stock solution may be diluted with a solvent (which may be the solvent of the stock solution or another solvent miscible therewith).

In some embodiments, the substituted chromones of the present disclosure with varying R groups may preferentially interact with specific PFASs. For example, the R groups may be chosen to selectively interact with perfluorooctanoic acid or other PFAS environmental contaminant. Accordingly, some embodiments may involve exposing substituted chromones to a water sample (e.g., drinking water, waste water effluent from a chemical, manufacturing, or nuclear plant, effluent from a water treatment plant, and the like, an extract from a water sample, extracts from soil samples, and the like) and determining the presence or absence of specific PFASs and/or determining a concentration of the specific PFASs. As used herein, the term "extract" refers to the solvent and dissolved/dispersed chemicals after treating a sample with the solvent. For example, a soil sample may be washed with DMSO and the DMSO extract may be analyzed for ions according to one or more methods described herein.

Figure 3A:
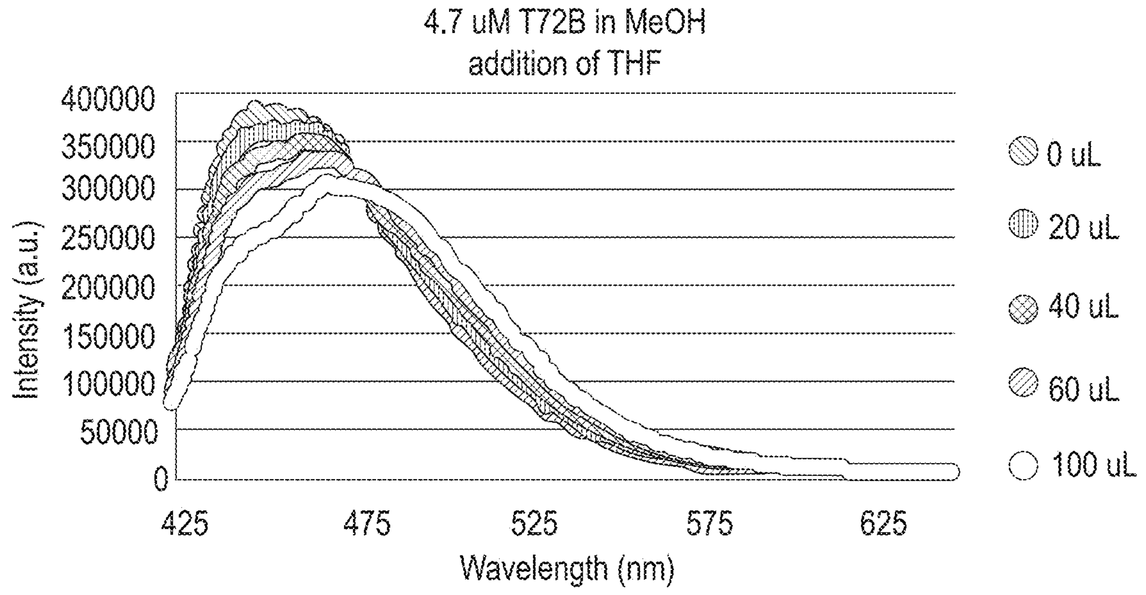
FIG. 3(*a*)-(*c*) illustrates fluorescent spectra of fluorophore of the present disclosure at varying concentrations of PFOA (perfluorooctanoic acid).
Figure 3B:
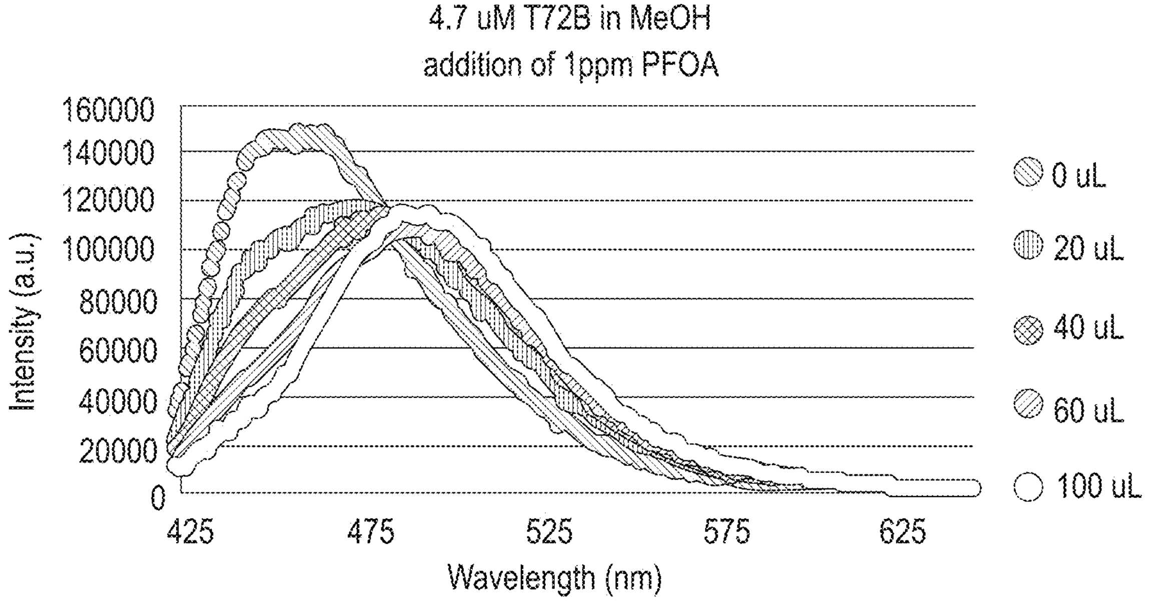
Figure 3C:
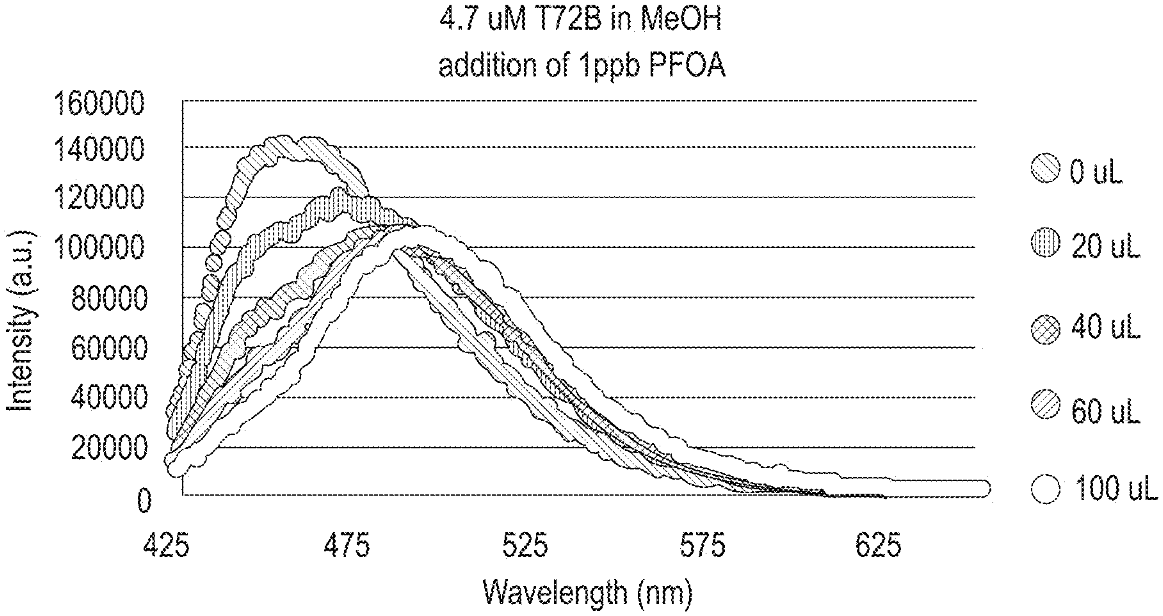
Figure 4A:
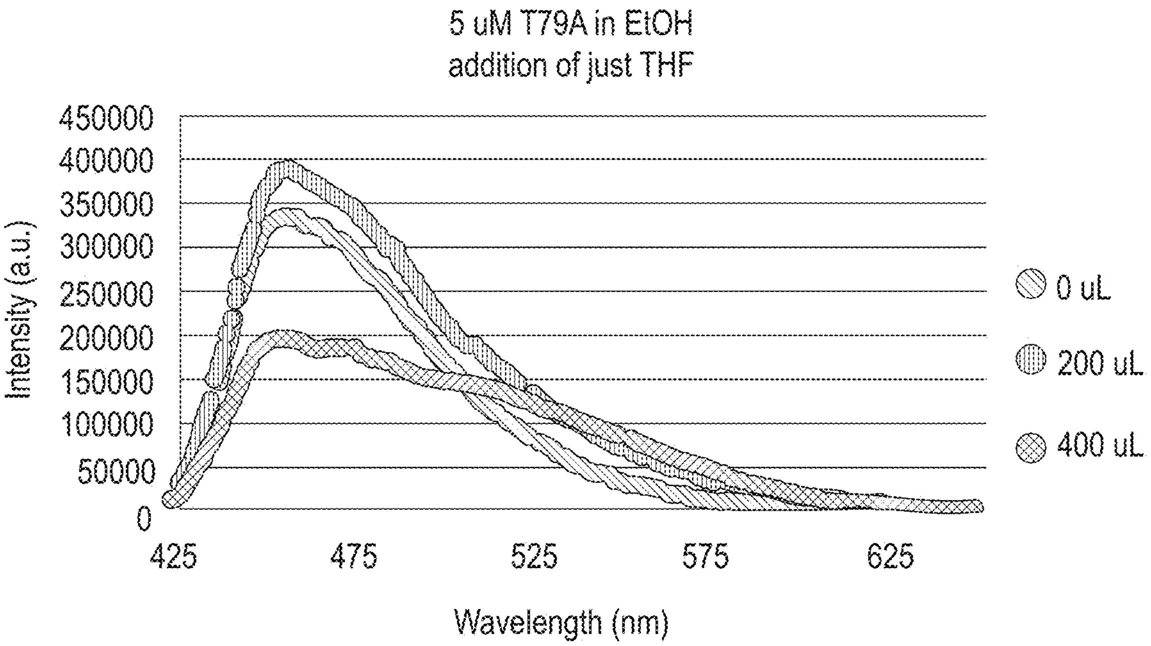
FIG. 4 illustrates fluorescent spectra for perfluorinated derivatives of the present disclosure.
Figure 4B:
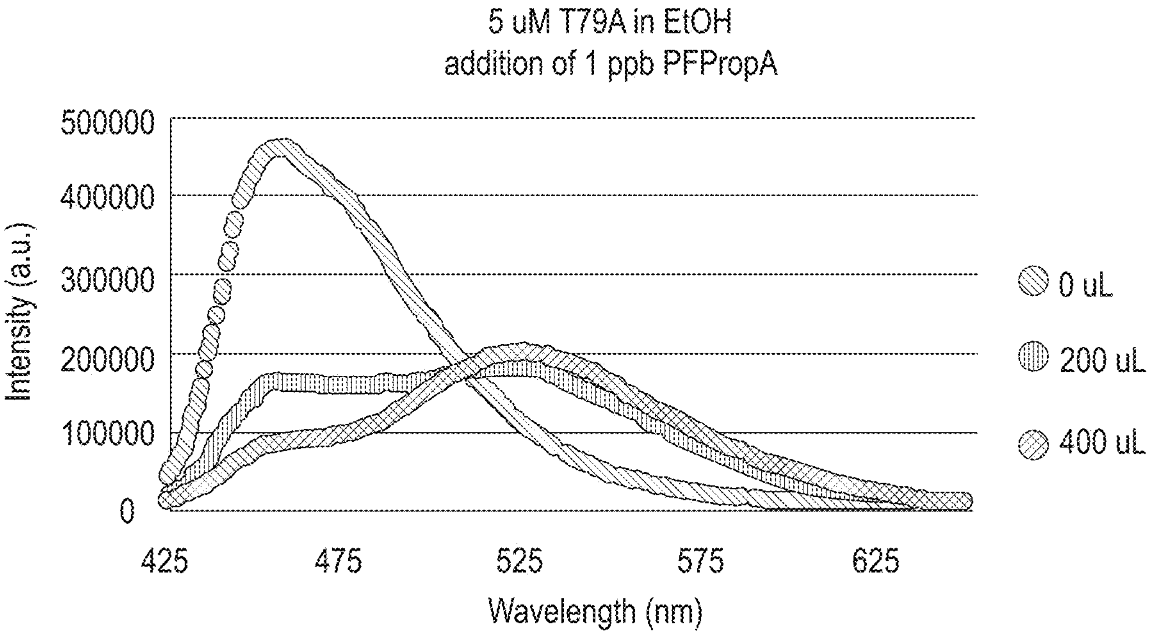
Figure 4C:
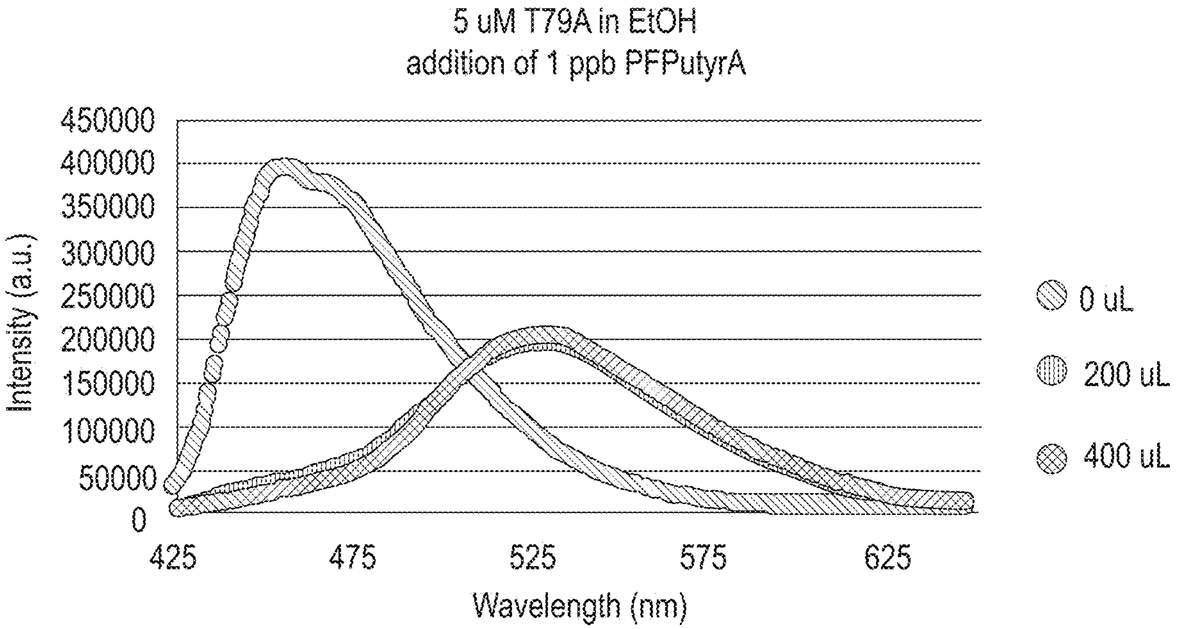
Figure 4D:
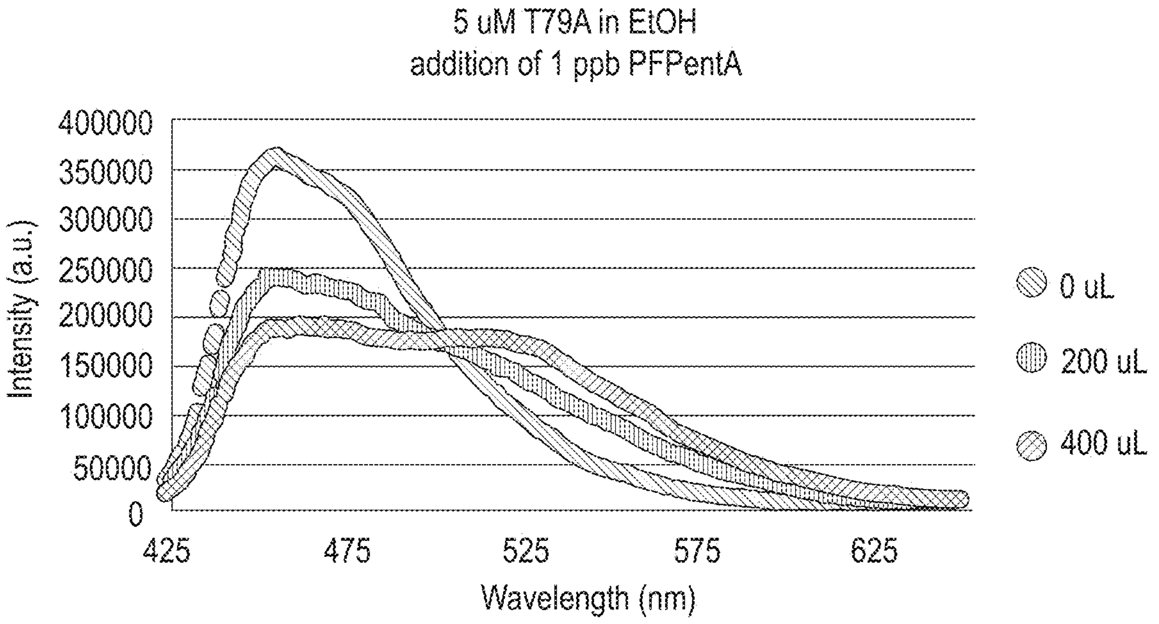
Figure 4E:
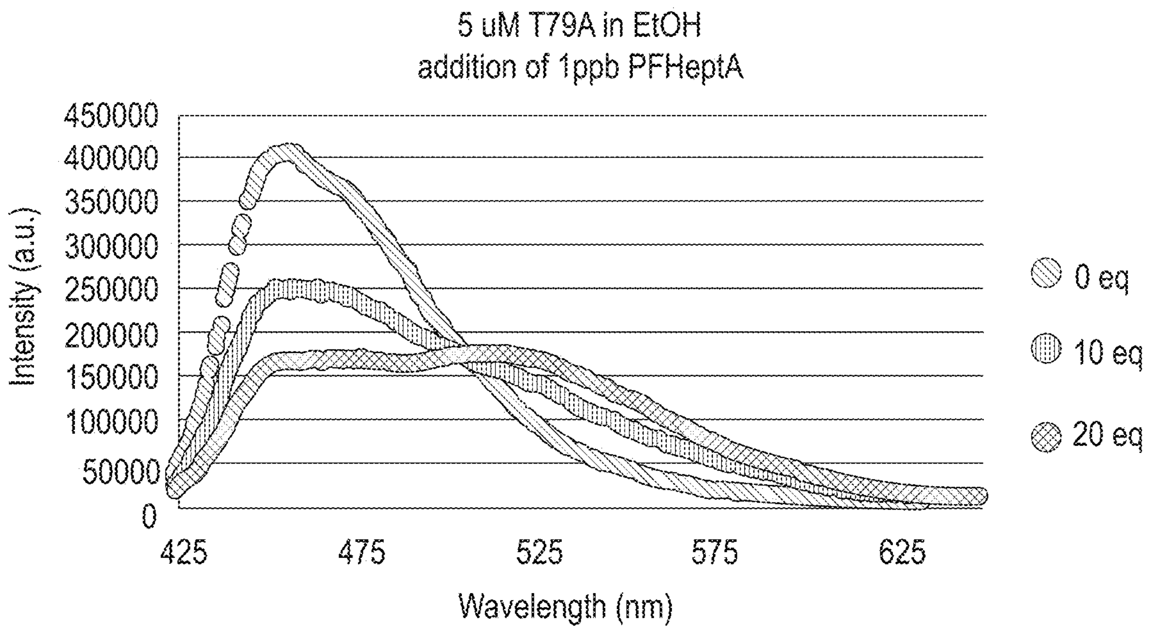

In addition to the R groups of the substituted chromones being chosen for a desired selectivity to specific PFASs, the solvent for the substituted chromones may also affect changes to the fluorescent properties. Exemplary solvents may include, but are not limited to, water, methanol, ethanol, tetrahydronfuran, acetone, dimethylformamide, acetonitrile, dimethyl sulfoxide, ethyl acetate, and miscible combinations thereof. For example, PFOA and other related derivatives have excellent solubility in THF. For example, when detecting PFASs, the solvent for the chromone may be 100% MeOH or EtOH. In some instances, the pH of the solvent may be adjusted, which may also affect the changes to the fluorescent properties of the substituted chromones. FIG. 3(*a*)-(*c*) shows the fluorescent spectra for Compound 8 and PFOA. Using ~5 μM solution of the fluorophore, different volumes of 1 ppm and 1 ppb PFOA (0-100 uL) were added to 1 mL of Compound 8. The subsequent solutions where then diluted to 5 mL using MeOH. FIGS. 3(*b*) and 3(*c*) clearly show that 1 ppm and 1 ppb concentrations can be detected. FIG. 3(*a*) is a THE control experiment. By simply adding 20 μL of the PFOA solutions a clear color change is observed, however, addition of 20 μL of THE causes no change in the fluorescence. Compound 9 was found to have similar results (data not shown), and both Compounds 8 and 9 are effective at detecting down to ~1 ppb levels of PFOA. As shown in FIG. 4(*b*)-(*e*), 1 ppb solutions of PFASs from Table 2 were tested along with Compound 8, and upon addition of 200 μL of each, a clear fluorescent change was observed. Addition of 200 μL of THF alone resulted in no color change. (FIG. 4(*a*).)

Figure 5A:
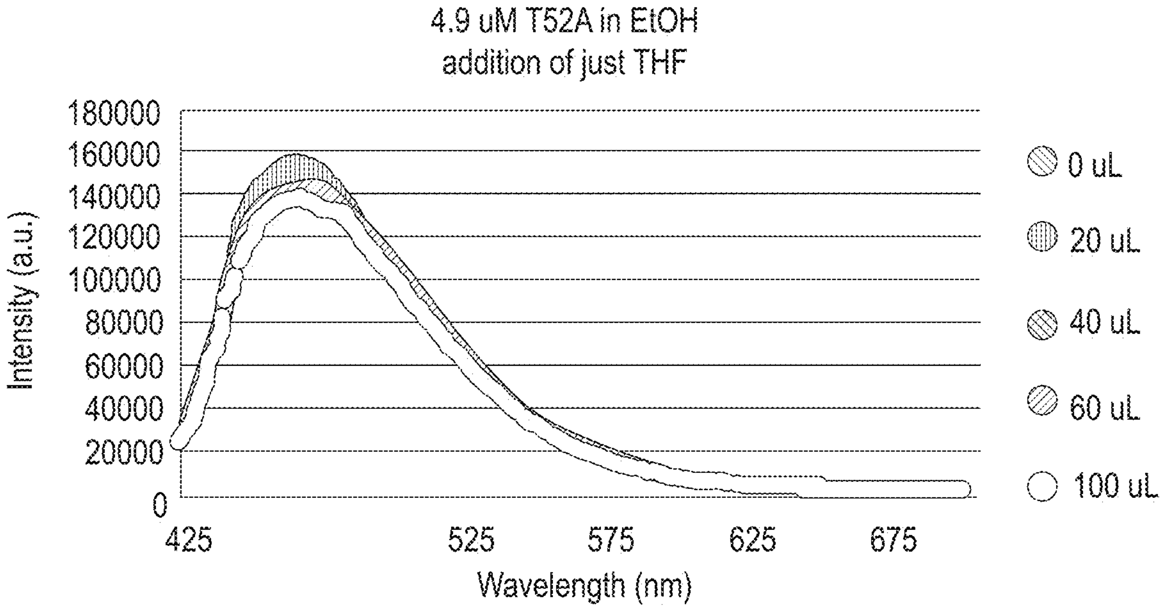
FIG. 5 illustrates fluorescence data obtained from a fluorophore of the present disclosure using a 1 ppb PFOA solution in THF.
Figure 5B:
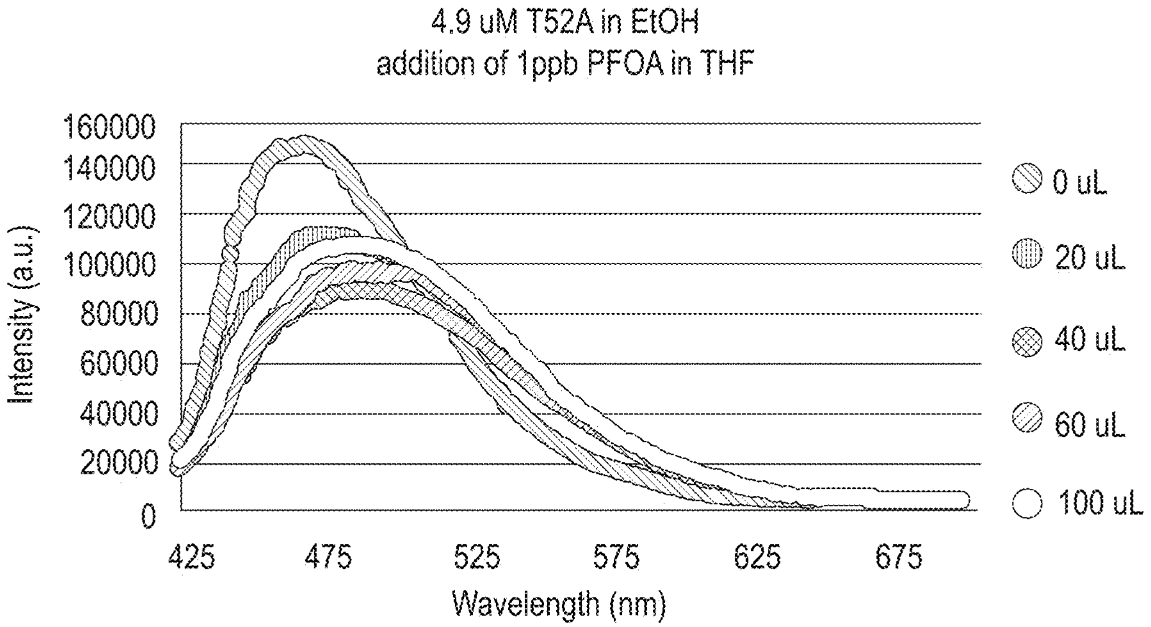
Figure 6A:
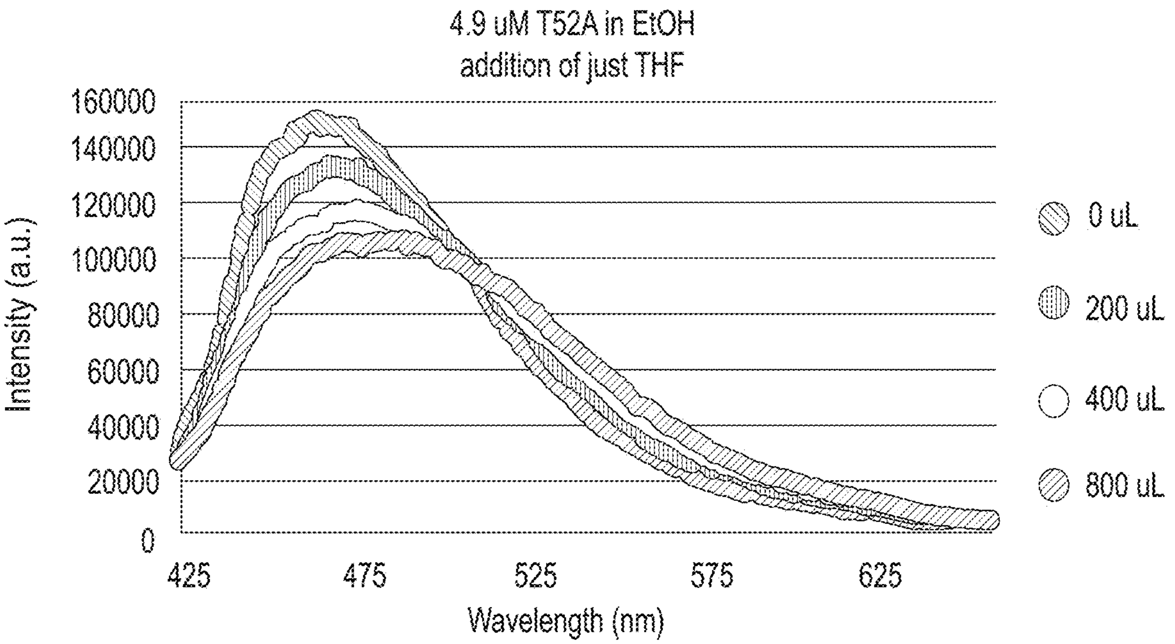
FIG. 6 illustrates the PFOA limits of detection of an exemplary fluorophore of the present disclosure.
Figure 6B:
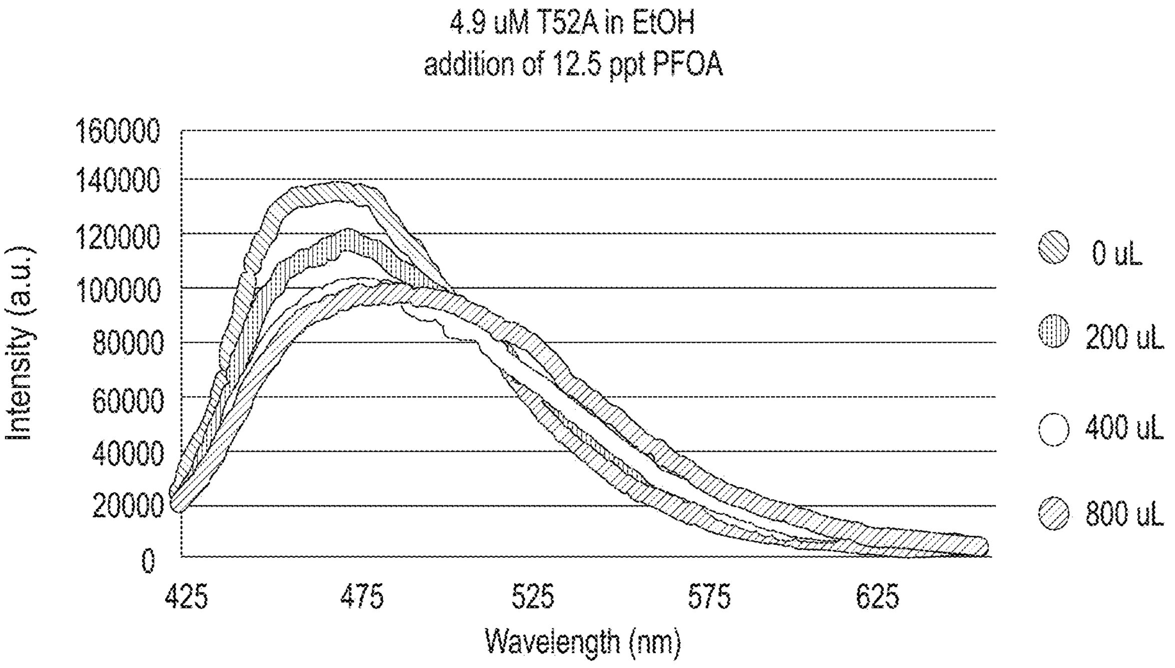
Figure 6C:
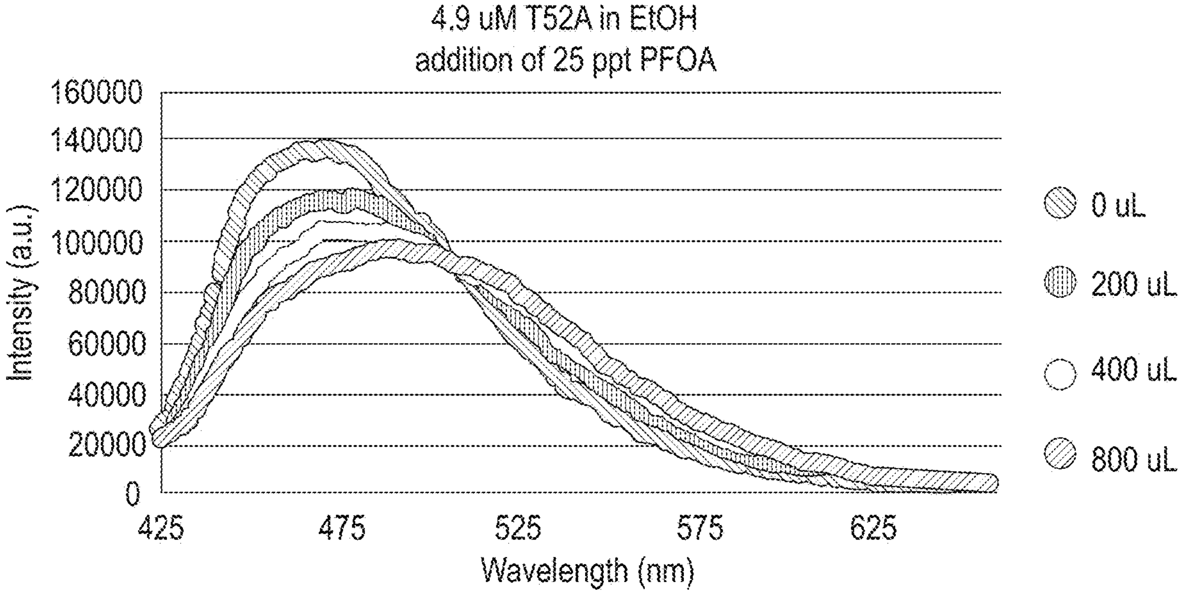
Figure 6D:
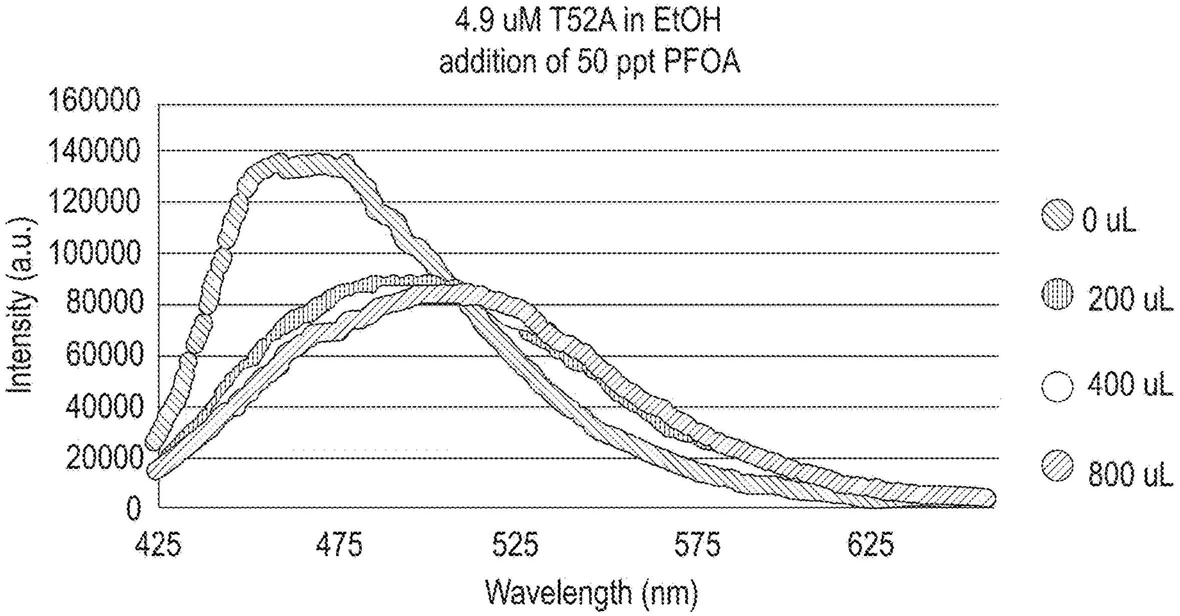
Figure 6E:
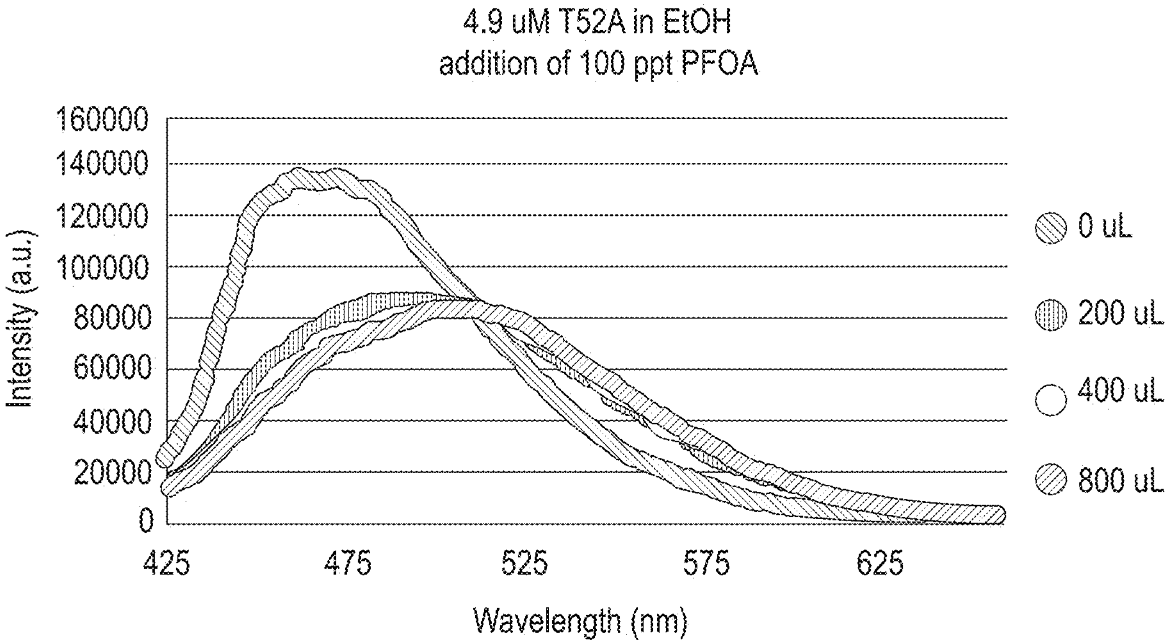
Figure 6F:
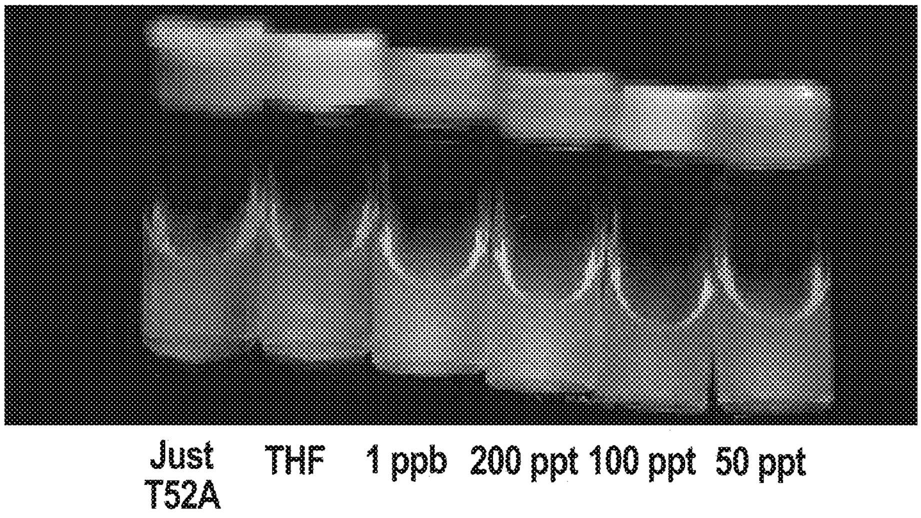

FIG. 5 represents the fluorescence data obtained using a 1 ppb PFOA solution in THF with Compound 4 as the fluorophore. It was observed very quickly that Compound 4 was an exemplary embodiment. As shown, there is a very apparent color change upon a 20 μL addition, while THF does not affect fluorescence.

Compound 4 was also observed to undergo a fluorescence color change upon addition of 500 and 250 ppt PFOA solutions. FIG. 6 highlights the detection limit. By comparing the THF control (FIG. 6(*a*)), it is clear that 100 ppt (FIG. 6(*e*)) and 50 ppt (FIG. 6(*d*)) solutions create a distinct fluorescence shift upon addition of 200 μL of each solution. A fluorimeter is not needed to observe this change in fluorescence. FIG. 6(*f*) shows the visual color differences between the fluorophore Compound 4, and Compound 4 plus 100 μL of THF, and varying concentrations of PFOA (100 μL aliquots added). As evidenced in FIG. 6, this method is a very quick, simple and inexpensive detection method for perfluorinated compounds.

Figure 7A:
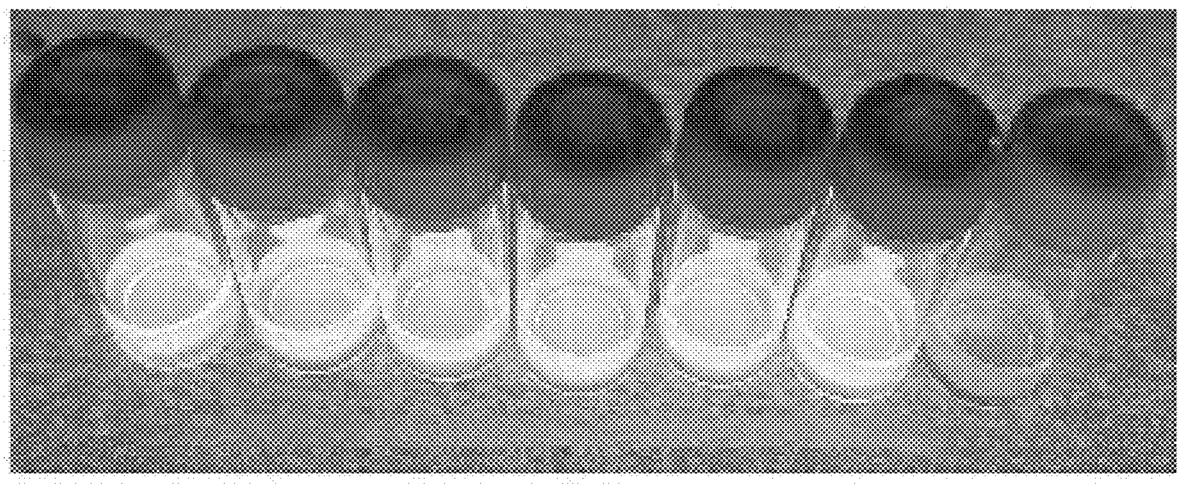
FIG. 7 illustrates the result of adding perfluorinated derivatives directly to a solution containing an exemplary fluorophore of the present disclosure.
Figure 7B:
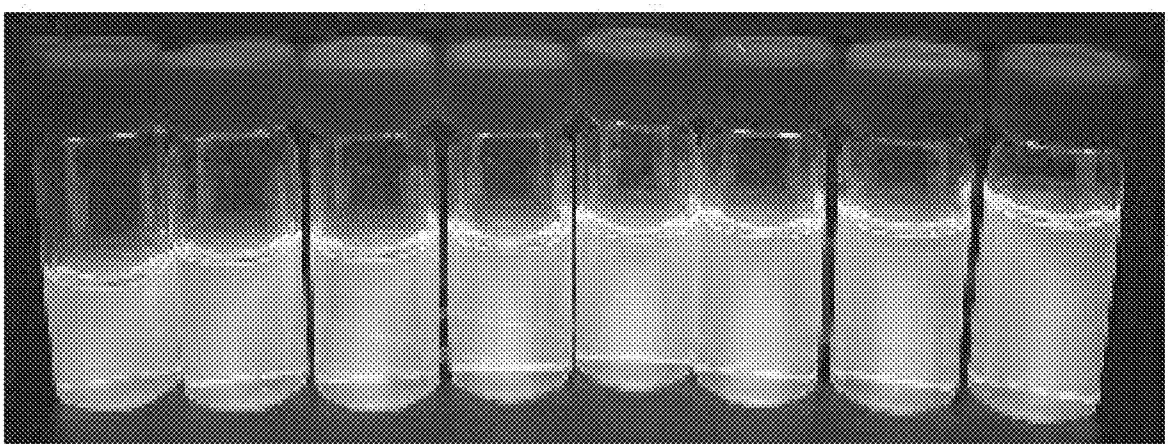

The fluorophores of the present disclosure are well suited for visual detection of PFASs. FIG. 7 shows that higher concentrations of Compound 4 in alcohol solvents results in a different color of fluorescence (compare the left vial of FIG. 6(*f*) to the left vial of FIGS. 7(*a*) and 7(*b*)), attributable to differing aggregates in higher and lower concentration solutions. Lower and higher concentrations of Compound 4 have been observed to work equally well in the detection of PFASs.

FIG. 7(*a*) shows the result of simply adding 1 ppb perfluorinated derivatives directly to the fluorophore solution (0.1 mM fluorophore). An immediate color change is observed after addition of 5 μL of liquid compounds, or a few crystals of solid compounds. The blank vial in FIG. 7(*a*) is Compound 4 in MeOH, 3C is perfluoropropionic acid, 4C is perfluorobutyric acid, 5C is perfluoropentanoic acid, 7C is perfluoroheptanoic acid, 8C is PFOA, and 4C sulf. acid is perfluorobutane sulfonic acid.

FIG. 7(*b*) shows the visual outcome of adding 100 ppt PFOA in THE in varying μL aliquots (0 μL, 20 μL, 40 μL, 60 μL, 100 μL, 200 μL, 300 μL and 400 μL). An evident color change is observed after only 20 μL are added, and the color different increases in intensity upon the addition of larger aliquots.

Figure 8A:
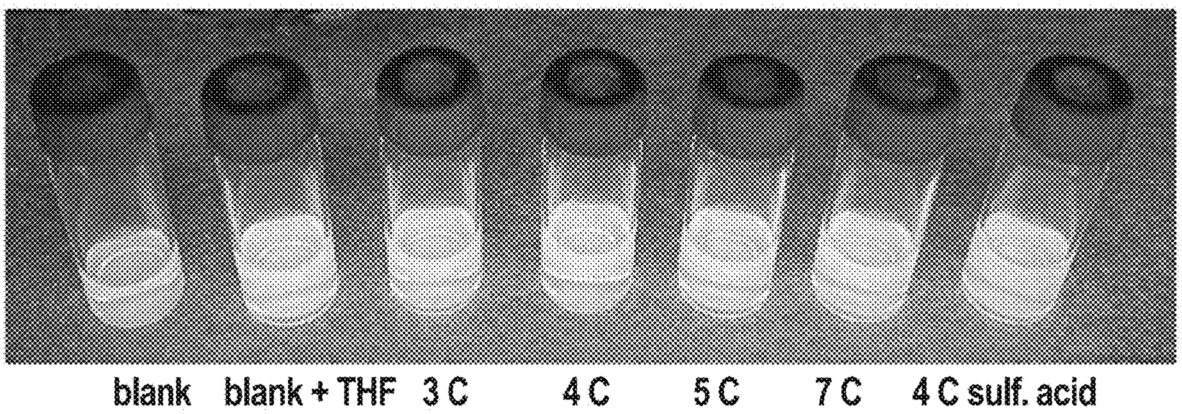
FIG. 8 shows the effectiveness of an exemplary fluorophore of the present disclosure at detecting various perfluorinated derivates.
Figure 8B:
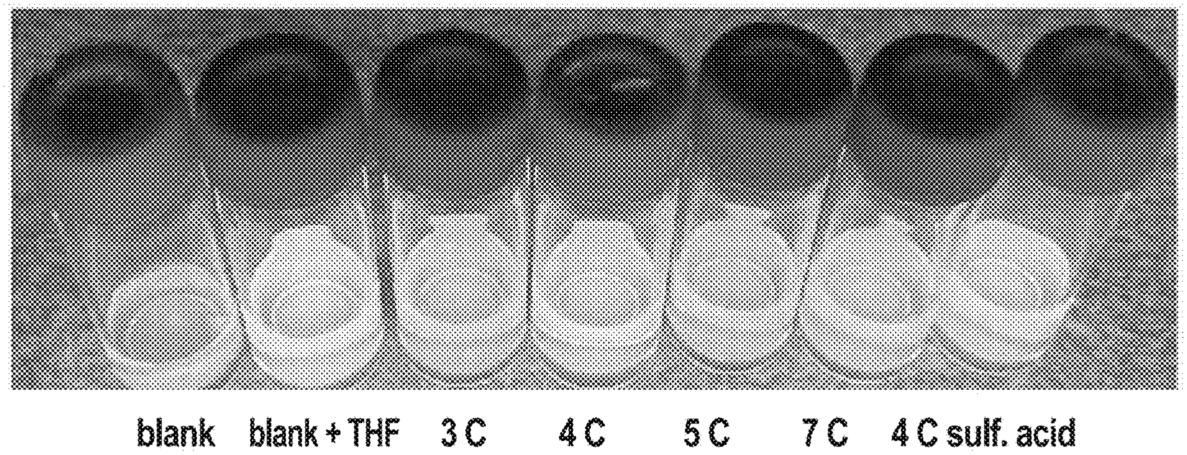

FIG. 8 shows the effectiveness of Compound 4 at detecting various perfluorinated derivatives. FIG. 8(*a*) shows the result of adding a 1 ppb solution to the Compound 4 fluorophore. A clear color change is observed for all of the perfluorinated derivates (a 200 μL aliquot was added to 500 μL of fluorophore). FIG. 8(*b*) shows the results of pushing the detection limit to 100 ppt. Fluorophores of the present disclosure are successful at detecting perfluorinated compounds down to 100 ppt concentrations or lower. In FIG. 8(*a*), 0.1 mM of Compound 4 was used to visually detect 1 ppb of a perfluorinated derivative. In both FIGS. 8(*a*) and 8(*b*), blank is Compound 4 in MeOH, 3C is perfluoropropionic acid, 4C is perfluorobutyric acid, 5C is perfluoropentanoic acid, 7C is perfluoroheptanoic acid, 8C is PFOA and 4C sulf. acid is perfluorobutane sulfonic acid. In FIG. 8(*b*), 0.1 mM of Compound 4 was used to visually detect 100 ppt of perfluorinated drivatives.

The substituted chromones described herein have unique flexibility and tailorability as fluorophores, and may be used in a variety of assays and corresponding kits and methods. For example, a kit may include (1) substituted chromones and dissolved in one or more solvents and (2) a set of instructions for analyzing the presence/absence of one or more PFASs, analyzing the concentration of one or more PFASs, or analyzing both. Included with the set of instructions, or separate therefrom, may be a table, graph, color chart reference, or other mathematical representation for correlating a change in one or more fluorescence properties to the concentration of one or more PFASs.

To facilitate a better understanding of the embodiments described herein, the following examples of various representative embodiments are given. In no way should the following examples be read to limit, or to define, the scope of the present disclosure.

Embodiments of the present disclosure include, but are not limited to, Embodiment A, Embodiment B, Embodiment C, and Embodiment D.

Embodiment A. A method comprising exposing a substituted chromone according to Compound 1 to a sample, wherein R1 is methyl acetate, methoxy, or methyl (2,2- dimethyl) acetate, R2 is 4-methylbenzoyl, 4-methoxybenzoyl, naphthalene-1-carbonyl, naphthalene-2-carbonyl, 4-phenylbenzoyl, or a perfluoroalkyl sulfonic acid compound wherein the alkyl is C5-C12, R3 is hydrogen, methoxy, bromo, chloro, fluoro, methyl, ethyl, or isopropyl, R4 is hydrogen, methoxy, bromo, chloro, fluoro, methyl, ethyl, or isopropyl, R5 is hydrogen, methoxy, bromo, chloro, fluoro, methyl, ethyl, or isopropyl, and R6a-e are any of hydrogen, methoxy, bromo, chloro, fluoro, methyl, ethyl, or isopropyl, taking a fluorescence measurement of the sample after exposure to the substituted chromone; and determining a presence or absence of one or more per- or polyfluoroalkyl hydrocarbons (PFAS), a concentration of the one or more PFAS in the sample, or both based on the fluorescence measurement.

Embodiment B. A method comprising exposing a substituted chromone according to Compound 2 to a sample, wherein R1 is methyl acetate, methoxy, or methyl (2,2-dimethyl) acetate, R2 is 4-methylbenzoyl, 4-methoxybenzoyl, naphthalene-1-carbonyl, naphthalene-2-carbonyl, 4-phenylbenzoyl, or a perfluoroalkyl sulfonic acid compound wherein the alkyl is C5-C12, R3 is hydrogen, methoxy, bromo, chloro, fluoro, methyl, ethyl, or isopropyl, R4 is hydrogen, methoxy, bromo, chloro, fluoro, methyl, ethyl, or isopropyl, R5 is hydrogen, methoxy, bromo, chloro, fluoro, methyl, ethyl, or isopropyl, and R6a-e are any of hydrogen, methoxy, bromo, chloro, fluoro, methyl, ethyl, or isopropyl, taking a fluorescence measurement of the sample after exposure to the substituted chromone; and determining a presence or absence of one or more per- or polyfluoroalkyl hydrocarbons (PFAS), a concentration of the one or more PFAS in the sample, or both based on the fluorescence measurement.

Embodiment C. A method comprising exposing a substituted chromone according to Compound 3 to a sample, wherein R1 is methyl acetate, methoxy, or methyl (2,2-dimethyl) acetate, R2 is 4-methylbenzoyl, 4-methoxybenzoyl, naphthalene-1-carbonyl, naphthalene-2-carbonyl, 4-phenylbenzoyl, or a perfluoroalkyl sulfonic acid compound wherein the alkyl is C5-C12, R3 is hydrogen, methoxy, bromo, chloro, fluoro, methyl, ethyl, or isopropyl, R4 is hydrogen, methoxy, bromo, chloro, fluoro, methyl, ethyl, or isopropyl, R5 is hydrogen, methoxy, bromo, chloro, fluoro, methyl, ethyl, or isopropyl, and R6a-e are any of hydrogen, methoxy, bromo, chloro, fluoro, methyl, ethyl, or isopropyl, taking a fluorescence measurement of the sample after exposure to the substituted chromone; and determining a presence or absence of one or more per- or polyfluoroalkyl hydrocarbons (PFAS), a concentration of the one or more PFAS in the sample, or both based on the fluorescence measurement.

Embodiment D. A composition comprising Compound 1, wherein R1 is methyl acetate, methoxy or methyl (2,2-dimethyl) acetate, R2 is 4-methylbenzoyl, 4-methoxybenzoyl, naphthalene-1-carbonyl, 4-phenylbenzoyl, a perfluoroalkyl sulfonic acid compound wherein the alkyl is C5-C12, R3 is hydrogen, methoxy, bromo, chloro, fluoro, methyl, ethyl, or isopropyl, R4 is hydrogen, methoxy, bromo, chloro, fluoro, methyl, ethyl, or isopropyl, R5 is hydrogen, methoxy, bromo, chloro, fluoro, methyl, ethyl, or isopropyl, and R6a-e is any of hydrogen, methoxy, bromo, chloro, fluoro, methyl, ethyl, or isopropyl.

Embodiments A-D may have one or more of the following additional elements in any combination:

Element 1: wherein Compound 1 is dissolved in a solvent.

Element 2: wherein Compound 1 is disposed on a test strip.

Element 3: wherein the fluorescence measurement is a first fluorescence measurement; wherein the method further comprises taking a second fluorescence measurement of the sample occurs before exposing the substituted chromone; and wherein determining the presence or absence of the one or more PFAS in the sample, the concentration of the one or more PFAS in the sample, or both based on a comparison of the first and second fluorescence measurements.

Element 4: wherein taking the fluorescence measurement of the sample involves exposing the sample to a 365 nm wavelength source and visually inspecting fluorescence from the sample.

Element 5: wherein determining the presence or absence of the one or more PFAS in the sample, the concentration of the one or more PFAS in the sample, or both is based on a comparison of the fluorescence measurement and a color chart reference.

Element 6: wherein the one or more PFAS comprise one or more selected from the group consisting of: perfluorooctanoic acid, perfluoroheptanoic acid, perfluoropentanoic acid, perfluorobutyric acid, perfluoropropionic acid, perfluorobutyric sulfonic acid, perfluorooctanesulfonyl chloride, undecafluoro-2-methyl-3-oxahexanoic acid, and any combination thereof.

Element 7: wherein the sample is from drinking water; ground water; or a waste water effluent from a chemical, manufacturing, or nuclear plant.

Element 8: wherein the sample is an extract from a soil sample.

Element 9: wherein Compound 1 is

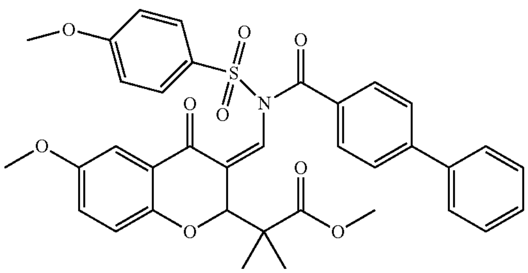

.

Element 10: wherein Compound 1 is

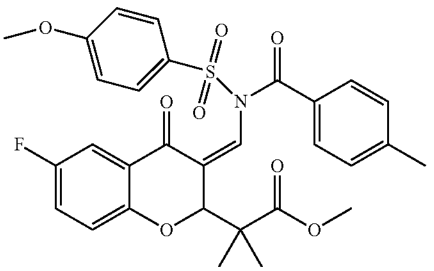

.

Element 11: wherein Compound 1 is

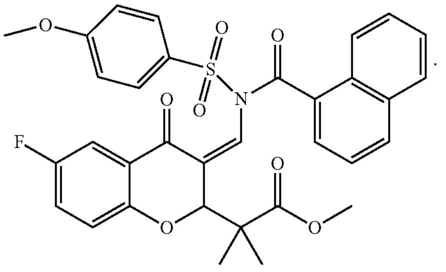 [SMILES: COC(=O)C(C)(C)C1Oc2ccc(F)cc2C(=O)/C1=C\N(C(=O)c1cccc2ccccc12)S(=O)(=O)c1ccc(OC)cc1]

Element 12: wherein Compound 1 is

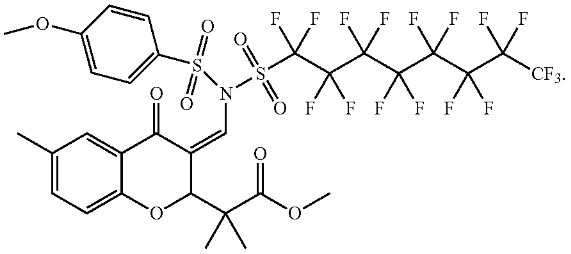 [SMILES: COC(=O)C(C)(C)C1Oc2ccc(C)cc2C(=O)/C1=C\N(S(=O)(=O)c1ccc(OC)cc1)S(=O)(=O)C(F)(F)C(F)(F)C(F)(F)C(F)(F)C(F)(F)C(F)(F)C(F)(F)C(F)(F)F]

Element 13: wherein Compound 2 is dissolved in a solvent.

Element 14, wherein Compound 2 is disposed on a test strip.

Element 15: wherein the fluorescence measurement is a first fluorescence measurement; wherein the method further comprises taking a second fluorescence measurement of the sample occurs before exposing the substituted chromone; and wherein determining the presence or absence of the one or more PFAS in the sample, the concentration of the one or more PFAS in the sample, or both based on a comparison of the first and second fluorescence measurements.

Element 16: wherein taking the fluorescence measurement of the sample involves exposing the sample to a 365 nm wavelength source and visually inspecting fluorescence from the sample.

Element 17: wherein determining the presence or absence of the one or more PFAS in the sample, the concentration of the one or more PFAS in the sample, or both is based on a comparison of the fluorescence measurement and a color chart reference.

Element 18: wherein the one or more PFAS comprise one or more selected from the group consisting of: perfluorooctanoic acid, perfluoroheptanoic acid, perfluoropentanoic acid, perfluorobutyric acid, perfluoropropionic acid, perfluorobutyric sulfonic acid, perfluorooctanesulfonyl chloride, undecafluoro-2-methyl-3-oxahexanoic acid, and any combination thereof.

Element 19: wherein the sample is from drinking water; ground water; or a waste water effluent from a chemical, manufacturing, or nuclear plant.

Element 20: wherein the sample is an extract from a soil sample.

Element 21: wherein Compound 3 is dissolved in a solvent.

Element 22: wherein Compound 3 is disposed on a test strip.

Element 23: wherein the fluorescence measurement is a first fluorescence measurement; wherein the method further comprises taking a second fluorescence measurement of the sample occurs before exposing the substituted chromone; and wherein determining the presence or absence of the one or more PFAS in the sample, the concentration of the one or more PFAS in the sample, or both based on a comparison of the first and second fluorescence measurements.

Element 24: wherein taking the fluorescence measurement of the sample involves exposing the sample to a 365 nm wavelength source and visually inspecting fluorescence from the sample.

Element 25: wherein determining the presence or absence of the one or more PFAS in the sample, the concentration of the one or more PFAS in the sample, or both is based on a comparison of the fluorescence measurement and a color chart reference.

Element 26: wherein the one or more PFAS comprise one or more selected from the group consisting of: perfluorooctanoic acid, perfluoroheptanoic acid, perfluoropentanoic acid, perfluorobutyric acid, perfluoropropionic acid, perfluorobutyric sulfonic acid, perfluorooctanesulfonyl chloride, undecafluoro-2-methyl-3-oxahexanoic acid, and any combination thereof.

Element 27: wherein the sample is from drinking water; ground water; or a waste water effluent from a chemical, manufacturing, or nuclear plant.

Element 28: wherein the sample is an extract from a soil sample.

Element 29: wherein the composition is

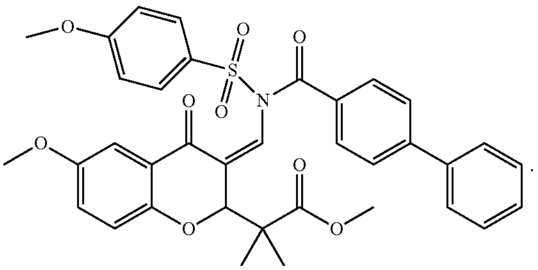 [SMILES: COC(=O)C(C)(C)C1Oc2ccc(OC)cc2C(=O)/C1=C\N(C(=O)c1ccc(-c2ccccc2)cc1)S(=O)(=O)c1ccc(OC)cc1]

Element 30: wherein the composition is

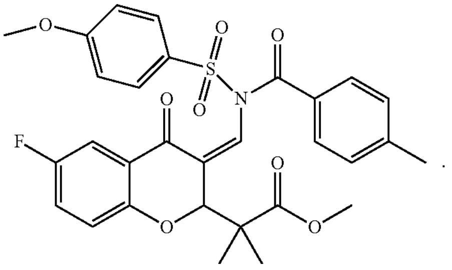

Element 31: wherein the composition is

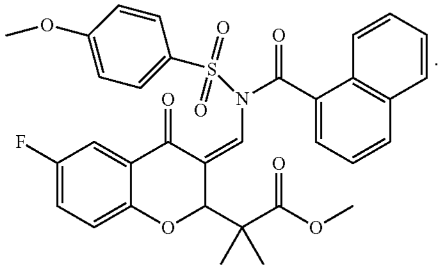 [SMILES: COC(=O)C(C)(C)C1Oc2ccc(F)cc2C(=O)/C1=C\N(C(=O)c1cccc2ccccc12)S(=O)(=O)c1ccc(OC)cc1]

Element 32: wherein the composition is

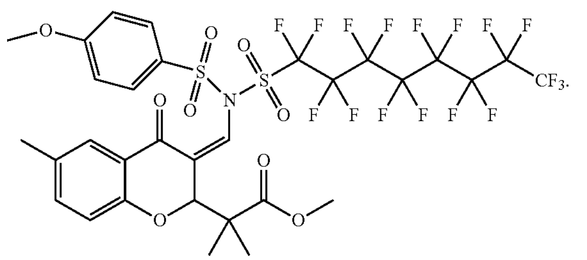 [SMILES: COC(=O)C(C)(C)C1Oc2ccc(C)cc2C(=O)/C1=C\N(S(=O)(=O)c1ccc(OC)cc1)S(=O)(=O)C(F)(F)C(F)(F)C(F)(F)C(F)(F)C(F)(F)C(F)(F)C(F)(F)C(F)(F)F]

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present invention. It is noted that, as used in this specification and the appended claims, the singular forms "a," "an," and "the," include plural references unless expressly and unequivocally limited to one reference. As used herein, the term "include" and its grammatical variants are intended to be non-limiting, such that recitation of items in a list is not to the exclusion of other like items that can be substituted or added to the listed items.

Any patent, patent application, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method comprising:

exposing a substituted chromone according to Compound 1 to a sample, wherein $R_1$ is methyl acetate, methoxy, or methyl (2,2-dimethyl) acetate, $R_2$ is 4-methylbenzoyl, 4-methoxybenzoyl, naphthalene-1-carbonyl, naphthalene-2-carbonyl, 4-phenylbenzoyl, or a perfluoroalkyl sulfonic acid compound wherein the alkyl is $C_5$-$C_{12}$, $R_3$ is hydrogen, methoxy, bromo, chloro, fluoro, methyl, ethyl, or isopropyl, $R_4$ is hydrogen, methoxy, bromo, chloro, fluoro, methyl, ethyl, or isopropyl, $R_5$ is hydrogen, methoxy, bromo, chloro, fluoro, methyl, ethyl, or isopropyl, and $R_{6a-e}$ are any of hydrogen, methoxy, bromo, chloro, fluoro, methyl, ethyl, or isopropyl, Compound 1

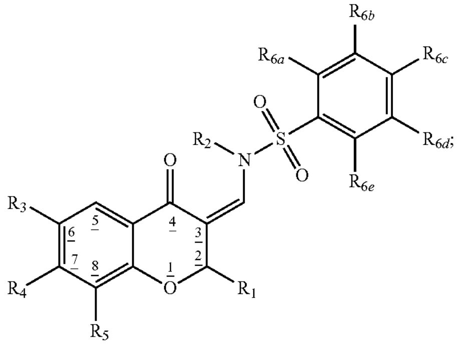

taking a fluorescence measurement of the sample after exposure to the substituted chromone; and determining a presence or absence of one or more per- or polyfluoroalkyl hydrocarbons (PFAS), a concentration of the one or more PFAS in the sample, or both based on the fluorescence measurement.

2. The method of claim 1, wherein Compound 1 is dissolved in a solvent.

3. The method of claim 1, wherein Compound 1 is disposed on a test strip.

4. The method of claim 1, wherein the fluorescence measurement is a first fluorescence measurement; wherein the method further comprises taking a second fluorescence measurement of the sample occurs before exposing the substituted chromone; and wherein determining the presence or absence of the one or more PFAS in the sample, the concentration of the one or more PFAS in the sample, or both based on a comparison of the first and second fluorescence measurements.

5. The method of claim 1, wherein taking the fluorescence measurement of the sample involves exposing the sample to a 365 nm wavelength source and visually inspecting fluorescence from the sample.

6. The method of claim 1, wherein determining the presence or absence of the one or more PFAS in the sample, the concentration of the one or more PFAS in the sample, or both is based on a comparison of the fluorescence measurement and a color chart reference.

7. The method of claim 1, wherein the one or more PFAS comprise one or more selected from the group consisting of: perfluorooctanoic acid, perfluoroheptanoic acid, perfluoropentanoic acid, perfluorobutyric acid, perfluoropropionic acid, perfluorobutyric sulfonic acid, perfluorooctanesulfonyl chloride, undecafluoro-2-methyl-3-oxahexanoic acid, and any combination thereof.

8. The method of claim 1, wherein the sample is from drinking water; ground water; or a waste water effluent from a chemical, manufacturing, or nuclear plant.

9. The method of claim 1, wherein the sample is an extract from a soil sample.

10. The method of claim 1, wherein Compound 1 is

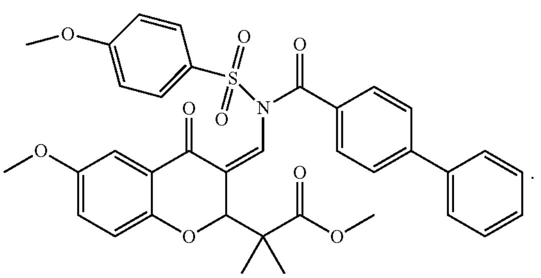 [SMILES: COC(=O)C(C)(C)C1Oc2ccc(OC)cc2C(=O)/C1=C\N(C(=O)c1ccc(-c2ccccc2)cc1)S(=O)(=O)c1ccc(OC)cc1]

11. The method of claim 1, wherein Compound 1 is

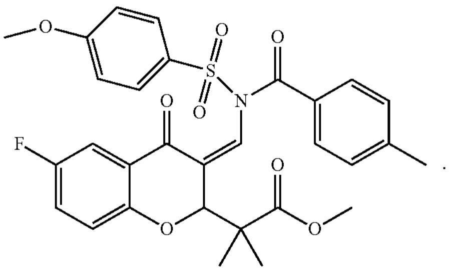

12. The method of claim 1, wherein Compound 1 is

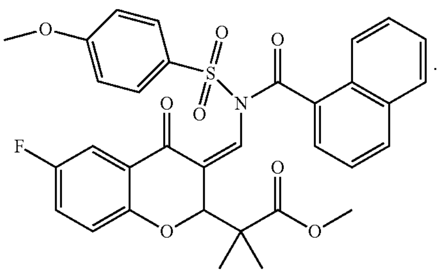 [SMILES: COC(=O)C(C)(C)C1Oc2ccc(F)cc2C(=O)/C1=C\N(C(=O)c1cccc2ccccc12)S(=O)(=O)c1ccc(OC)cc1]

13. The method of claim 1, wherein Compound 1 is

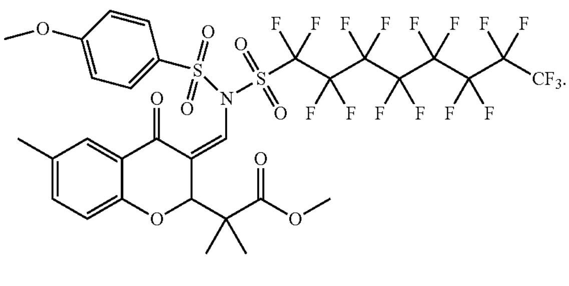 [SMILES: COC(=O)C(C)(C)C1Oc2ccc(C)cc2C(=O)/C1=C\N(S(=O)(=O)c1ccc(OC)cc1)S(=O)(=O)C(F)(F)C(F)(F)C(F)(F)C(F)(F)C(F)(F)C(F)(F)C(F)(F)C(F)(F)F]

14. A method comprising:

exposing a substituted chromone according to Compound 2 to a sample, wherein $R_1$ is methyl acetate, methoxy, or methyl (2,2-dimethyl) acetate, $R_2$ is 4-methylbenzoyl, 4-methoxybenzoyl, naphthalene-1-carbonyl, naphthalene-2-carbonyl, 4-phenylbenzoyl, or a perfluoroalkyl sulfonic acid compound wherein the alkyl is $C_5$-$C_{12}$, $R_3$ is hydrogen, methoxy, bromo, chloro, fluoro, methyl, ethyl, or isopropyl, $R_4$ is hydrogen, methoxy, bromo, chloro, fluoro, methyl, ethyl, or isopropyl, $R_5$ is hydrogen, methoxy, bromo, chloro, fluoro, methyl, ethyl, or isopropyl, and $R_{6a-e}$ are any of hydrogen, methoxy, bromo, chloro, fluoro, methyl, ethyl, or isopropyl, Compound 2

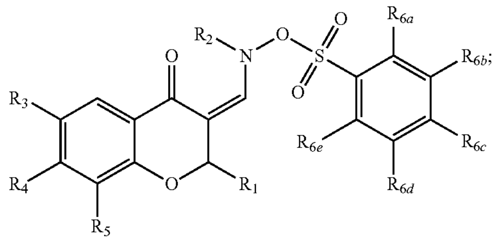

taking a fluorescence measurement of the sample after exposure to the substituted chromone; and determining a presence or absence of one or more per- or polyfluoroalkyl hydrocarbons (PFAS), a concentration of the one or more PFAS in the sample, or both based on the fluorescence measurement.

15. The method of claim 14, wherein Compound 2 is dissolved in a solvent.

16. The method of claim 14, wherein Compound 2 is disposed on a test strip.

17. The method of claim 14, wherein the fluorescence measurement is a first fluorescence measurement; wherein the method further comprises taking a second fluorescence measurement of the sample occurs before exposing the substituted chromone; and wherein determining the presence or absence of the one or more PFAS in the sample, the concentration of the one or more PFAS in the sample, or both based on a comparison of the first and second fluorescence measurements.

18. The method of claim 14, wherein taking the fluorescence measurement of the sample involves exposing the sample to a 365 nm wavelength source and visually inspecting fluorescence from the sample.

19. The method of claim 14, wherein determining the presence or absence of the one or more PFAS in the sample, the concentration of the one or more PFAS in the sample, or both is based on a comparison of the fluorescence measurement and a color chart reference.

20. The method of 14, wherein the one or more PFAS comprise one or more selected from the group consisting of: perfluorooctanoic acid, perfluoroheptanoic acid, perfluoropentanoic acid, perfluorobutyric acid, perfluoropropionic acid, perfluorobutyric sulfonic acid, perfluorooctanesulfonyl chloride, undecafluoro-2-methyl-3-oxahexanoic acid, and any combination thereof.

21. The method of claim 14, wherein the sample is from drinking water; ground water; or a waste water effluent from a chemical, manufacturing, or nuclear plant.

22. The method of claim 14, wherein the sample is an extract from a soil sample.

23. A method comprising:

exposing a substituted chromone according to Compound 3 to a sample, wherein $R_1$ is methyl acetate, methoxy, or methyl (2,2-dimethyl) acetate, $R_2$ is 4-methylbenzoyl, 4-methoxybenzoyl, naphthalene-1-carbonyl, naphthalene-2-carbonyl, 4-phenylbenzoyl, or a perfluoroalkyl sulfonic acid compound wherein the alkyl is $C_5$-$C_{12}$, $R_3$ is hydrogen, methoxy, bromo, chloro, fluoro, methyl, ethyl, or isopropyl, $R_4$ is hydrogen, methoxy, bromo, chloro, fluoro, methyl, ethyl, or isopropyl, $R_5$ is hydrogen, methoxy, bromo, chloro, fluoro, methyl, ethyl, or isopropyl, and $R_{6a-e}$ are any of hydrogen, methoxy, bromo, chloro, fluoro, methyl, ethyl, or isopropyl, Compound 3

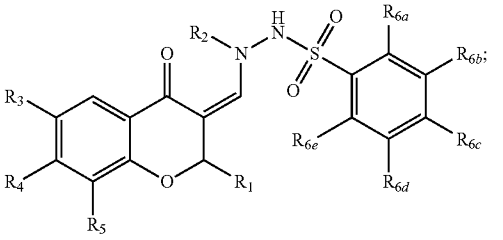

taking a fluorescence measurement of the sample after exposure to the substituted chromone; and determining a presence or absence of one or more per- or polyfluoroalkyl hydrocarbons (PFAS), a concentration of the one or more PFAS in the sample, or both based on the fluorescence measurement.

* * * * *